(12) United States Patent
Ikhlef et al.

(10) Patent No.: US 9,168,008 B2
(45) Date of Patent: Oct. 27, 2015

(54) COARSE SEGMENTED DETECTOR ARCHITECTURE AND METHOD OF MAKING SAME

(75) Inventors: Abdelaziz Ikhlef, Hartland, WI (US); Jeffrey Alan Kautzer, Pewaukee, WI (US)

(73) Assignee: General Electric Company, Schenectady, NY (US)

(*) Notice: Subject to any disclaimer, the term of this patent is extended or adjusted under 35 U.S.C. 154(b) by 779 days.

(21) Appl. No.: 13/288,138

(22) Filed: Nov. 3, 2011

(65) Prior Publication Data

US 2013/0114786 A1 May 9, 2013

(51) Int. Cl.
*A61B 6/03* (2006.01)
*G01N 23/04* (2006.01)
*A61B 6/06* (2006.01)
*A61B 6/00* (2006.01)

(52) U.S. Cl.
CPC ............... *A61B 6/032* (2013.01); *A61B 6/4266* (2013.01); *G01N 23/046* (2013.01); *A61B 6/06* (2013.01); *A61B 6/4035* (2013.01); *A61B 6/4411* (2013.01); *A61B 6/4435* (2013.01); *A61B 6/5205* (2013.01); *G01N 2223/419* (2013.01); *G01N 2223/639* (2013.01); *Y10T 29/49826* (2015.01)

(58) Field of Classification Search
CPC ............... A61B 6/4266; A61B 6/4411; G01N 2223/501
USPC .................. 250/363.05, 370.09–370.15, 394, 250/363.08, 370.11; 378/19
See application file for complete search history.

(56) References Cited

U.S. PATENT DOCUMENTS

| | | | |
|---|---|---|---|
| 4,338,521 A * | 7/1982 | Shaw et al. ............. | 250/370.11 |
| 5,991,357 A * | 11/1999 | Marcovici et al. ............. | 378/19 |
| 7,233,640 B2 | 6/2007 | Ikhlef et al. | |
| 7,564,940 B2 | 7/2009 | Mattson et al. | |
| 7,602,951 B2 | 10/2009 | Hsieh et al. | |
| 7,620,143 B2 | 11/2009 | Ikhlef et al. | |
| 7,825,370 B2 | 11/2010 | Ikhlef et al. | |
| 7,888,647 B2 | 2/2011 | Warner et al. | |
| 7,965,811 B1 * | 6/2011 | Gregerson et al. ................. | 378/4 |
| 2002/0054659 A1 * | 5/2002 | Okumura et al. ............. | 378/19 |
| 2004/0016885 A1 | 1/2004 | Ikhlef | |
| 2004/0017888 A1 * | 1/2004 | Seppi et al. ..................... | 378/57 |
| 2005/0111612 A1 | 5/2005 | Ikhlef et al. | |
| 2006/0289765 A1 | 12/2006 | Ikhlef et al. | |
| 2007/0086565 A1 | 4/2007 | Thompson et al. | |
| 2008/0310585 A1 | 12/2008 | Ikhlef et al. | |

(Continued)

FOREIGN PATENT DOCUMENTS

JP 2011141193 A * 7/2011

*Primary Examiner* — David J Makiya
*Assistant Examiner* — John Corbett
(74) *Attorney, Agent, or Firm* — Ziolkowski Patent Solutions Group, SC

(57) ABSTRACT

A CT system includes a rotatable gantry having an opening to receive an object to be scanned, the rotatable gantry having a detector mounting surface, an x-ray source attached to the gantry and configured to project an x-ray beam toward the object, a plurality of detector modules each mounted within one field-of-view (FOV) and mounted directly to the detector mounting surface of the rotatable gantry, a data acquisition system (DAS) configured to receive outputs from at least one of the plurality of detector modules, and a computer programmed to acquire projections of imaging data of the object from the DAS, and generate an image of the object using the imaging data.

17 Claims, 5 Drawing Sheets

(56) References Cited

U.S. PATENT DOCUMENTS

2009/0121146 A1* 5/2009 Luhta et al. .............. 250/370.11
2012/0076257 A1* 3/2012 Star-Lack et al. ................. 378/4
2012/0148015 A1 6/2012 Simon

* cited by examiner

COARSE SEGMENTED DETECTOR ARCHITECTURE AND METHOD OF MAKING SAME

BACKGROUND OF THE INVENTION

Embodiments of the invention relate generally to diagnostic imaging and, more particularly, to a method and apparatus of maintaining image quality while reducing system fabrication cost.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for rejecting scatter x-rays from the patient, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

Typically, the detector array is fabricated from a large number of detector modules that are each separately fabricated, tested, and installed into the detector array during assembly. For instance, in one design the detector array is fabricated from 57 modules, each having 16 channels along a channel direction of the detector array. The modules of known designs may include 8, 16, 32, 64, or more pixels in a slice direction of the detector array.

However, because of the complexity of the design of the modules: to include high density interconnects, array bonding of a backlit diode, underfill, and myriad other issues, the modules are very expensive to fabricate and test. And, as complexity increases, the possibility for yield losses during module fabrication and testing increases as well. Further, the modules that make up the detector array are aligned and positioned with a high degree of accuracy with respect to one another, typically on the order of microns are required. As such, the detector array is typically fabricated in a test bay as a stand-alone unit and then the unit is installed and tested in a larger assembly bay.

In addition, in some system designs or applications it may be desirable to reduce an amount of detector coverage along the slice direction (to, for instance 8 slices of coverage) in order to reduce system cost, enabling a cost tradeoff to be made between coverage and cost. However, in other system designs or applications it may be desirable to increase an amount of coverage along the slice direction (to, for instance 16, 64, or 256 slices as examples). As such, there are multiple configurations of designs that may be desired based on z-coverage and cost tradeoffs. Each detector design, though, includes different amounts of z coverage. That is, an 8-slice detector is typically designed from 8-slice detector components, a 16-slice detector is typically designed from 16-slice detector components, etc. . . . , resulting in a different system design for each amount of coverage that is desired. As such, there is typically not a lot commonality in designs of different slice coverage, resulting in separate components and assembly and test procedures for each unique design.

Thus, there are therefore not only myriad issues associated with fabrication and testing of individual detector modules, but overall system cost, complexity, and yield are also affected because of the different detector designs having differing amounts of z-coverage. And, in some markets, such as in the developing world, there is less need for a "high-end" imaging capability as such systems may be priced out of the market while providing functionality that is of less demand (such as 64 slice or 256 slice coverage). For instance, systems having 64-slice capability or greater are directed increasingly toward the desire to image a full organ in a single rotation. However, in many markets it is more desirable to have a much more basic scanning capability, with system cost a much more important driver than high-end scanning capability. In other words, in some markets it is desirable to have an option to purchase a system that is skewed toward low cost, with users willing to forego a more high-end scanning capability.

As such, there is a need to reduce cost and complexity of detector arrays in imaging application, particularly in system designs having a more limited amount of z-coverage that are directed toward a value end of the market. Therefore, it would be desirable to design an apparatus and method to reduce cost of a CT system, while providing a basic amount of detector coverage, system and performance capability.

BRIEF DESCRIPTION OF THE INVENTION

The invention is a directed method and apparatus for imaging using a cost effective, highly reliable, and serviceable module.

According to one aspect, a CT system includes a rotatable gantry having an opening to receive an object to be scanned, the rotatable gantry having a detector mounting surface, an x-ray source attached to the gantry and configured to project an x-ray beam toward the object, a plurality of detector modules each mounted within one field-of-view (FOV) and mounted directly to the detector mounting surface of the rotatable gantry, a data acquisition system (DAS) configured to receive outputs from at least one of the plurality of detector modules, and a computer programmed to acquire projections of imaging data of the object from the DAS, and generate an image of the object using the imaging data.

According to another aspect, a method of fabricating a CT system includes fabricating a gantry having a detector mounting surface, attaching an x-ray source to the gantry such that x-rays emit from the x-ray source and through the rotational axis, and attaching, within one field-of-view (FOV), each detector module directly to the detector mounting surface such that the x-rays also emit to the two or more detector modules.

According to yet another aspect, a CT detector module includes an electronics board, a first mounting surface, and a second mounting surface; wherein the first mounting surface is configured to be mounted directly onto a rotatable gantry of a CT system, the second mounting surface is configured such that the electronics board is mounted orthogonal with respect to x-rays emitted from an x-ray source that is positioned on the rotatable gantry.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION OF THE PREFERRED EMBODIMENT

The operating environment of the invention is described with respect to a eight and sixteen-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
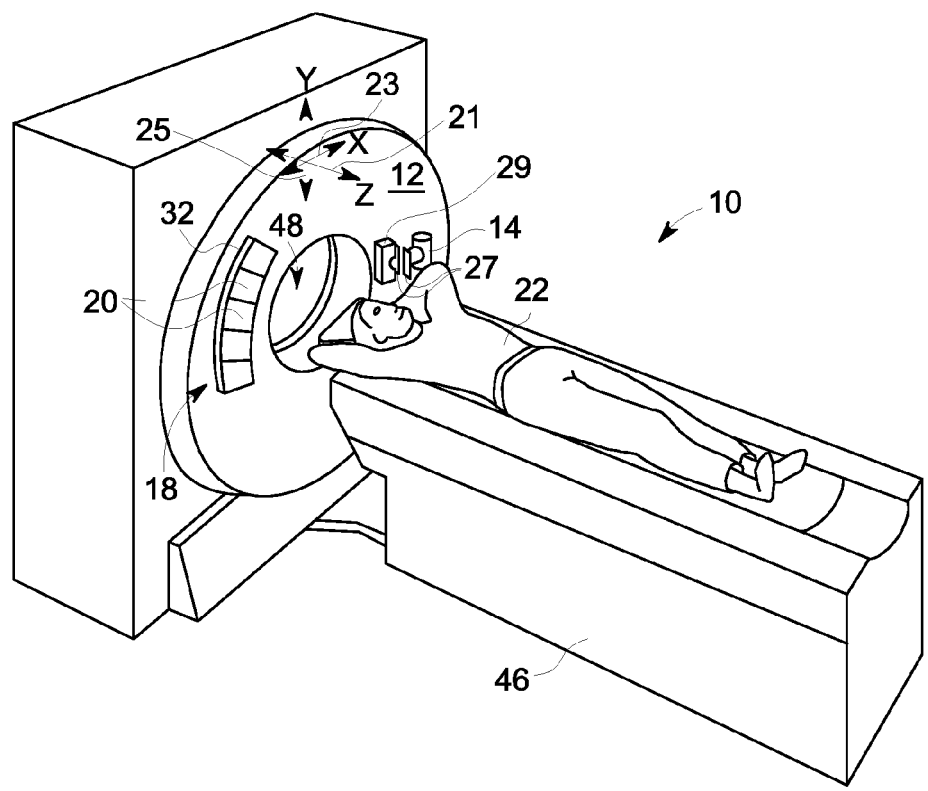
FIG. 1 is a pictorial view of a CT imaging system.
Figure 2:
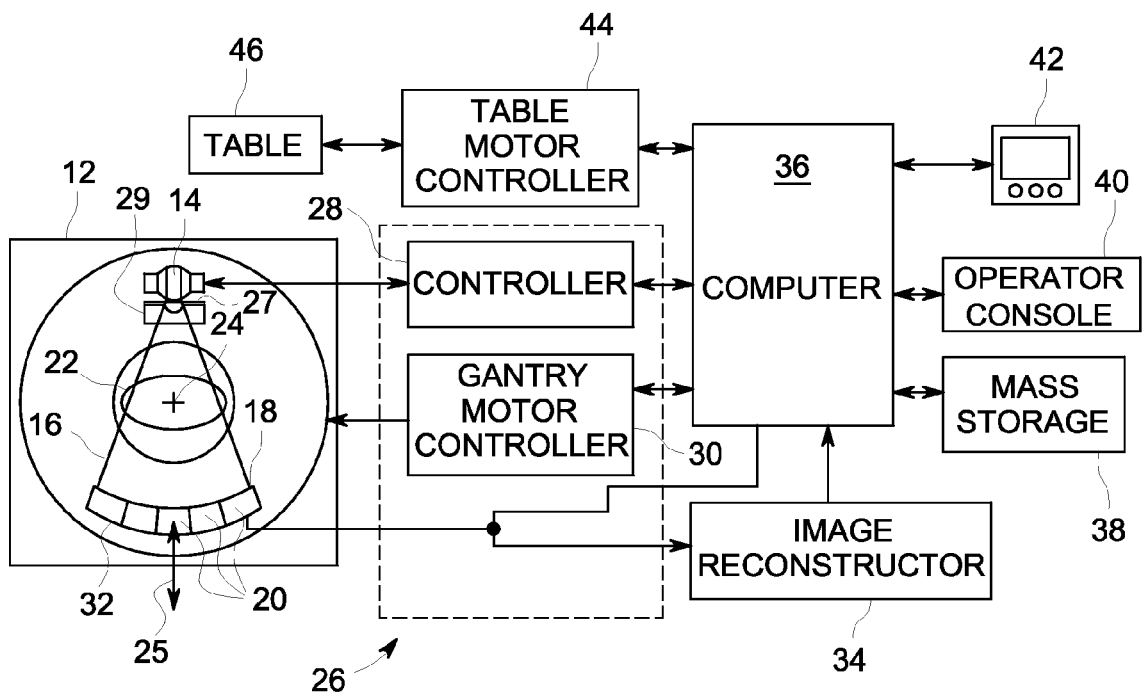
FIG. 2 is a block schematic diagram of the system illustrated in FIG. 1.

Referring to FIGS. 1 and 2, a computed tomography (CT) imaging system 10 is shown as including a rotatable gantry 12 representative of a "third generation" CT scanner. Rotatable gantry 12 has an x-ray source 14 that projects a beam of x-rays 16 toward a detector assembly 18 on the opposite side of the rotatable gantry 12. Imaging system 10 includes a pre-patient collimator 27 and a bowtie filter 29. Pre-patient collimator 27 is configured to control a beam width, in a z-direction and as known in the art, between x-ray source 14 and detector assembly 18. Detector assembly 18 is formed by a plurality of detectors 20 that are directly attached to rotatable gantry 12. The plurality of detectors 20 sense the projected x-rays 16 that pass through medical patient 22. Detectors 20 include a DAS 32 that converts the data from detectors 20 to digital signals for subsequent processing. Each detector 20 produces an analog electrical signal that represents the intensity of an impinging x-ray beam and hence the attenuated beam as it passes through the patient 22. During a scan to acquire x-ray projection data, rotatable gantry 12 and the components mounted thereon rotate about an axis of rotation 24.

Rotation of rotatable gantry 12 and the operation of x-ray source 14 are governed by a control mechanism 26 of CT system 10. Control mechanism 26 includes a controller 28 that provides power and timing signals to an x-ray source 14 as well as motion control for operation of pre-patient collimator 27 and bowtie filter 29, and control mechanism 26 includes a gantry motor controller 30 that controls the rotational speed and position of rotatable gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and rotatable gantry 12. Particularly, table 46 moves patients 22 through a gantry opening 48 of FIG. 1 in whole or in part.

As commonly understood in the art, patient 22 is generally translated along a z-direction 21, commonly referred to as a slice-direction, of rotatable gantry 12. As also commonly understood in the art, detector assembly 18 is caused to rotate circumferentially in a channel direction 23, of rotatable gantry 12. Thus, x-rays 16 travel generally in a direction 25 and through detector assembly 18 as they emit from x-ray source 14 and pass through patient 22.

As illustrated in FIGS. 1 and 2 and as will be further discussed, CT system 10 includes a plurality of detectors 20 that are mounted directly to rotatable gantry 12. And, although five modules 20 are illustrated therein, it is contemplated that less than or more than 5 modules may be included, dependent on desired field of view (FOV), according to the invention.

Figure 3:
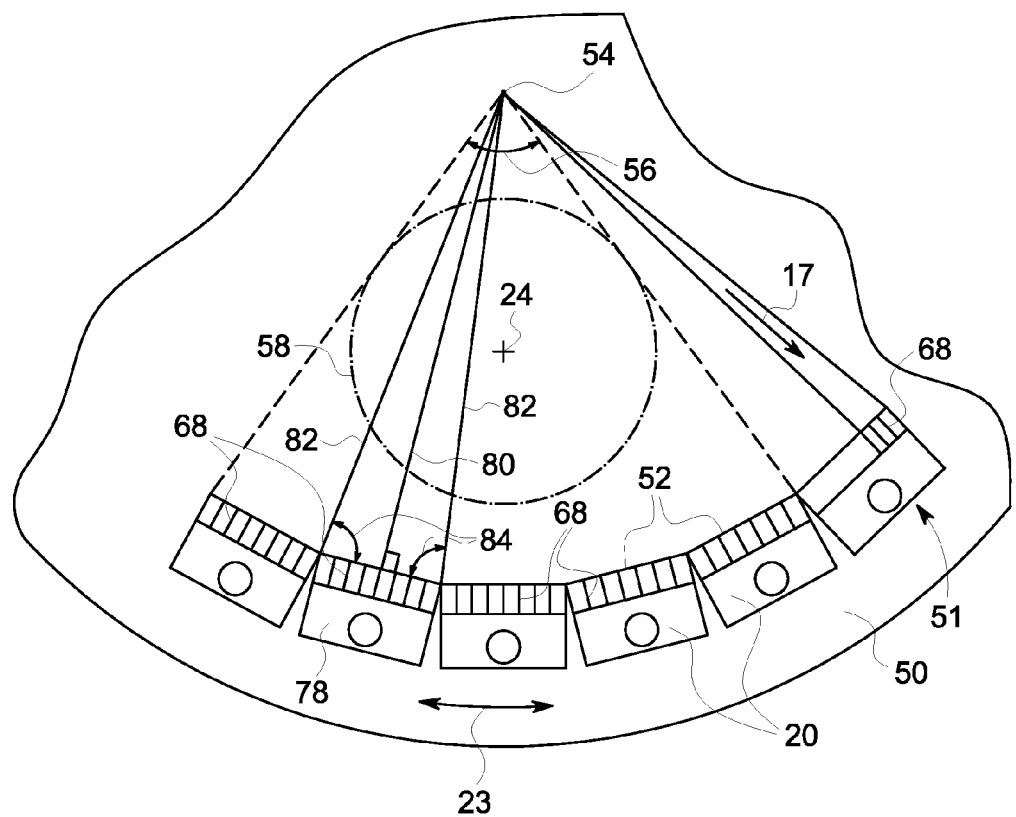
FIG. 3 is a plan view of a rotatable gantry according to an embodiment of the invention.
Figure 4:
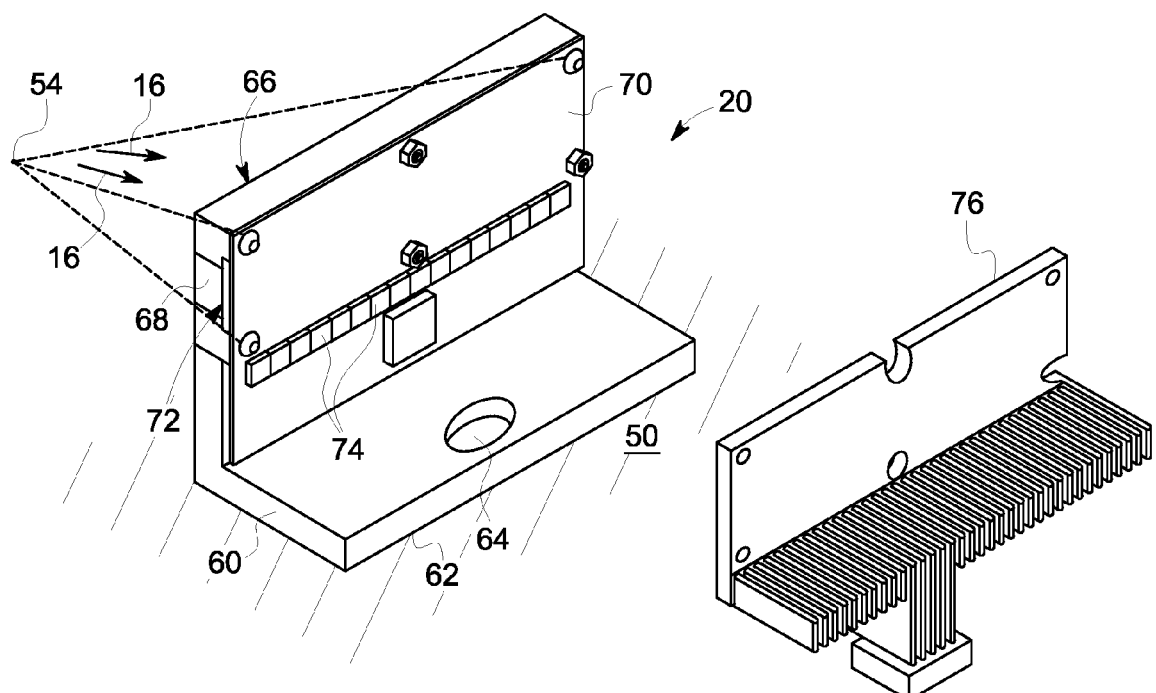
FIG. 4 is a perspective view of a perspective view of one module, according to an embodiment of the invention.

Referring now to FIG. 3, a plan view of rotatable gantry 12 includes a detector mounting surface 50 and five modules 20 that are attached directly thereto having collimator plates 68 that are generally fanned and angled such that they collimate x-rays emanating from a focal spot 54, as will be further described in FIG. 4. Detector mounting surface 50 includes a removable module 51 having its own collimator plates 68. Removable module 51 thereby serves as a reference for x-rays 17 that pass outside of a field-of-view (FOV) 58 and removable module 51 may include only a limited number of collimator plates 68, and corresponding detector elements, as illustrated. Thus, in contrast to a conventional system design where detector modules are attached to, for instance, a collimator assembly, which is then attached as a whole unit to a gantry, modules 20 of the present invention are attached directly to the rotatable gantry and are thus standalone units which may be separately fabricated, pre-tested and attached thereto, according to the invention. Such a modular design enables simple repair and replacement of individual modules, as opposed to having to remove an entire detector unit, having a plurality of detector modules attached thereto, as is conventionally done.

Each module 20 includes a surface 52 that is generally perpendicular to focal spot 54 that emanates from an x-ray tube (not shown), such as x-ray tube 14 illustrated in FIGS. 1 and 2. Circumferential coverage 56 of modules 20 defines FOV 58, which defines an imaging region over which imaging data may be obtained from modules 20 as rotatable gantry 12, that comprises detector mounting surface 50, and is rotated about axis of rotation 24. As will be further discussed, each module 20 includes an array of pixels in both the channel direction 23, and in the slice direction (direction 21 illustrated in FIG. 1). As such and as understood in the art, the total number of channels in channel direction 23 is a product of the number of channels in each module and the number of modules. Accordingly, it is contemplated that circumferential coverage 56 that defines FOV 58 is a function of a number of geometrical parameters related to rotatable gantry 12, including but not limited to the number of channels in each module 20 in channel direction 23, the pitch thereof, the number of modules 20 employed, and their placement with respect to focal spot 54, as examples.

Referring now to FIG. 4, a perspective view of one module 20 is illustrated, of the five modules 20 of FIGS. 1-3, positioned on detector mounting surface 50 with respect to focal spot 54, according to one embodiment of the invention. Module 20 includes an L-shaped bracket 60 having a planar module mounting surface 62 that is attachable to detector mounting surface 50 via, for instance, a bolt (not shown) through aperture 64. According to this embodiment, module mounting surface 62 is generally at a right angle to a surface 66 (surface 66 corresponds to surface 52 of FIG. 3, and is orthogonal to x-rays 16 passing from focal spot 54), toward which x-rays 16 emanate from focal spot 54. Likewise, module mounting surface 62 is orthogonal, in the illustrated embodiments, to rotational axis 24 of system 10. It is to be recognized that module mounting surface 62 need not be orthogonal to rotational axis 24, and that the angle therebetween may be varied based on the design of rotatable gantry 12 and the surfaces used to mount modules 20. However, the angle of L-shaped bracket 60 would change accordingly, so long as surfaces 52 are maintained generally orthogonal to x-rays 16 passing from focal spot 54.

Module 20 includes a collimator array 68 attached to L-shaped bracket 60 via bolts, screws, or other known methods. Collimator 68 is configured to reject scatter from the patient, corresponding to x-rays coming from angle outside the primary beam angle and collimate x-rays that emit toward module 20 from focal spot 54 using. For instance, high-density plates (such as tungsten) that are generally positioned in a fanned angle toward focal spot 54, as is known in the art. Module 20 includes an electronics board 70 attached to collimator 68 and L-shaped bracket 60, having mounted thereon a photodiode array and scintillator 72, as known in the art. According to the invention, photodiode array of photodiode array and scintillator 72 includes either a backlit photodiode array or a frontlit photodiode array. As understood in the art, a backlit photodiode array is configured to be electrically attached to a board, such as electronics board 70, such that electrical signals are read through the back side of the scintillator, whereas a frontlit photodiode array is read out from the front side using electrical traces positioned on the front side (i.e., toward the x-ray source).

Electronics board 70 also includes electrical components such as ASICS 74 and other components that comprise DAS 32. Electronics board 70 is, for instance, a printed circuit board (PCB) having multiple layers therein that enable readout from photodiode array and scintillator 72 to ASICS 74, and to an image reconstructor and/or computer (via a cable, not shown), as illustrated in FIG. 2. According to the invention, electronics board 70 may include a heat sink 76 attached thereto and thermally coupled to ASICS 74 and other components of electronics board 70.

Thus, referring to FIGS. 1-4, a plurality of modules 20 are attached directly to detector mounting surface 50 of rotatable gantry 12 and form FOV 58 therewith. As can be seen particularly in FIG. 1, when rotatable gantry 12 is rotated, detector mounting surface 50 thereof is generally orthogonal to axis of rotation 24. Modules 20 formed as such are formed of L-shaped bracket 60, which enables modules 20 to be mounted directly to detector mounting surface 50 while presenting a surface 52/66 that is orthogonal to x-rays 16 that emit from focal spot 54.

X-rays 16 are caused to emit from focal spot 54, toward surface 52/66, pass into the scintillator of photodiode array and scintillator 72. Resultant photons pass to photodiode array of photodiode array and scintillator 72, where electrical signals are generated and read out using electronics board 70.

Figure 5:
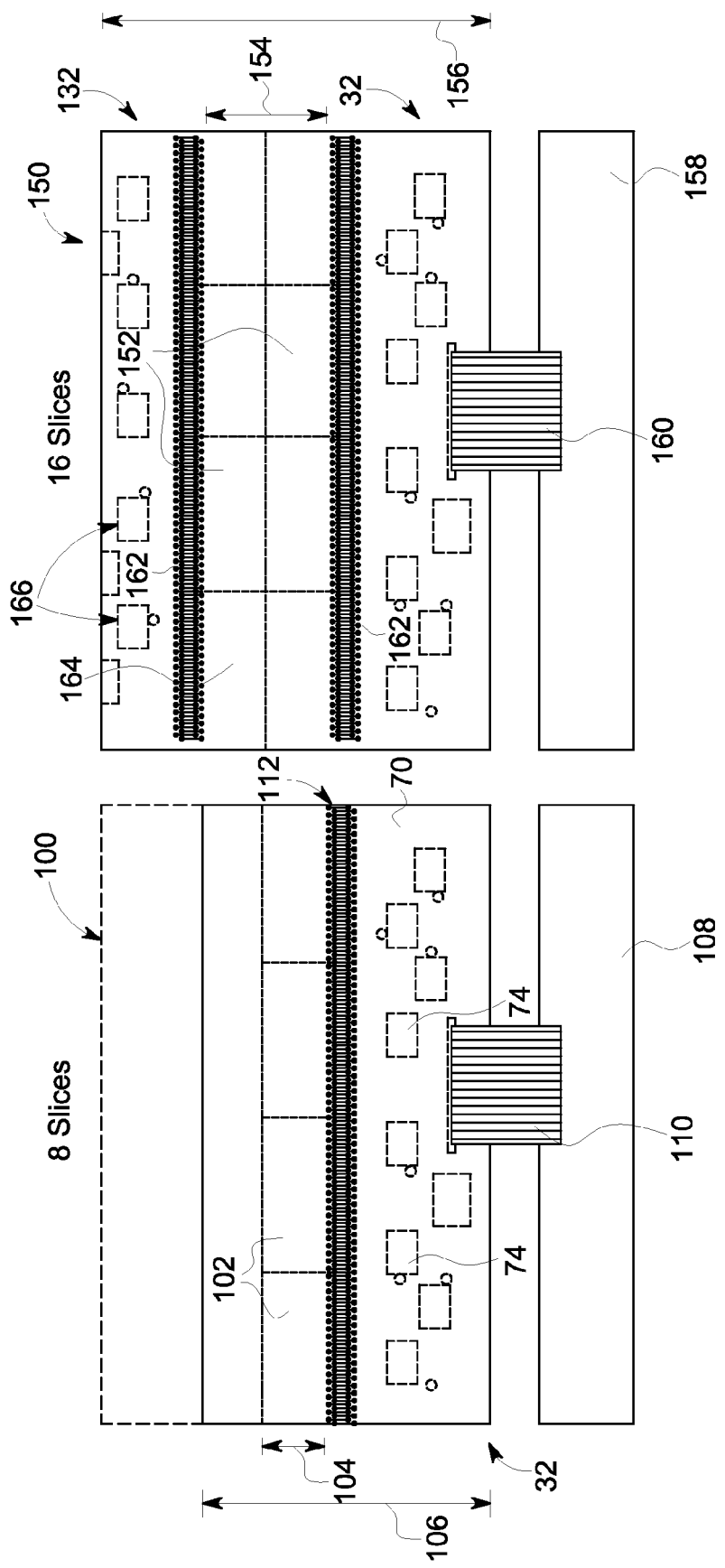
FIG. 5 is a plan view of a module having both an 8-slice and a 16-slice configuration.

According to the invention, module 20 is configured so that either an 8-slice or a 16-slice can be included therewith. That is, during fabrication, either 8-slice or 16-slice components may be selected, based on the desired design that is being fabricated. In other words, module 20 is designed in order that common components may be used for system 10, except for the components that are used in module(s) 20. Such an arrangement is illustrated in FIG. 5. Referring to FIG. 5, module 20 is illustrated as a plan view of surface 52 of FIG. 3 and surface 66 of FIG. 4 (but without collimator 68 and without a corresponding scintillator placed on the diode array, for simplicity of illustration purposes).

In the 8-slice illustration 100, diode arrays 102 (here illustrated as frontlit diodes) are positioned on electronics board 70, having positioned thereon (illustrated in phantom to show that they are on a side of electronics board 70 that is opposite the surface being viewed) DAS 32 that includes ASICS 74 and other electronic components. Diode arrays 102 define a total amount of z-coverage 104 over 8-slices (i.e., 8 pixels of slice information), which corresponds to z-direction 21 as shown in FIG. 1. As illustrated, electronics board 70 includes a total width in z-direction 106 and includes a backplane 108 that receives digital signals from DAS 32 via a flex cable 110. Wirebonds 112 are positioned, in this embodiment that shows frontlit diodes, to electrically connect diode arrays 102 to electronics board 70. Although not illustrated, it is to be understood that collimator 68 of FIG. 4 is configured having a z-width of coverage that corresponds to total amount of z-coverage 104 and 8 slices of pixel coverage.

In another arrangement of this embodiment, still referring to FIG. 5, 16-slice configuration 150 includes diode arrays 152 that are positioned on electronics board 70. In this arrangement, a total amount of z-coverage 154 over 16-slices (i.e., 16 pixels of slice information), which corresponds to z-direction 21. As illustrated in this configuration, and in contrast to 8-slice illustration 100, electronics board 70 includes a total width in z-direction 156 that is different from total width in z-direction 106 of 8-slice illustration 100, and includes a backplane 158 that receives digital signals from DAS 32 via a flex cable 160. Wirebonds 162, in this arrangement, electrically connect diode arrays 152 to electronics board 70 on both sides of the arrays. Although not illustrated, it is to be understood that collimator 68 of FIG. 4 is configured having a z-width of coverage that corresponds to total amount of z-coverage 154 and 16 slices of pixel coverage.

As such, illustrations 100 and 150 of FIG. 5 include both 8 and 16 slice configurations that may be incorporated into system 10, and components thereof, of FIGS. 1-4. That is, module 20 may be configured to accommodate an 8 or 16 slice collimator, 8 slices of pixel coverage with a scintillator/diode array combination, and corresponding DAS components. In the 8-slice arrangement, electronics board 70 is narrower in width 106 than that of the 16-slice arrangement, requiring two types of board 70 for each respective configuration. However, the invention is not to be so limited and it is contemplated that a single design of board 70 may be included that includes accommodation of either an 8 or 16 slice arrangement. For instance, according to this embodiment, a single board 70 may be included such as that illustrated for 16-slice configuration 150, but it may be depopulated for an 8-slice arrangement. Thus, board 70 having total width in z-direction 21 156 may be used for either arrangement, but in the 8-slice arrangement, additional diode arrays 164 and additional DAS components 166 may be foregone such that only an 8-slice arrangement is fabricated. Thus, in this arrangement, a single design of components, including but not limited to electronics board 70 and collimator 68, may be used to accommodate either an 8 or a 16 slice configuration. Accordingly, the total number of components is decreased, significantly reducing overall manufacturing costs, while enabling fabrication of either system.

As such, the design of module 20, according to the invention, enables a simple design where parts commonality may be simplified and a total number of parts can be reduced. Embodiments include separate boards 70 and other corresponding components for each slice configuration, and embodiments include a single dedicated board 70 and other corresponding components that may include more than one configuration. Further and as stated, the invention is not to be limited to 8 and 16 slice configurations, and may include any combination of slice options for system fabrication, such as 16/32 slice options, 32/64 slice options, and the like. Also, each single module 20 can be separately tested during manufacturing, because of the modular design thereof. It is also expected that the collimator can be fabricated having an improved tolerance and therefore quality because the collimator is fabricated as a modular unit. Further, because DAS functionality can be increased having with more functionality built into the FPGA than in a conventional module. The modules 20 disclosed herein are self-structuring and stand-alone modules, removing the need for external support rails or other methods—allowing modules 20 to be separately tested and then directly attached to the rotatable gantry, according to the invention. Because the module includes the complete image chain (Collimator, Scintillator, Diode, A/D, FPGA, Thermal management circuit), it can be fully tested before assembly on the detector and qualified against system specifications.

Still further, the invention is not limited to only two slice options (i.e., 8 and 16 slices), but is applicable to additional combinations of slice options. That is, multiple board 70 types may be included that are specific to a configuration that may be simply and easily be incorporated into the manufacturing process, to provide yet additional manufacturing flexibility into a single overall system configuration while providing multiple slice options. For instance, referring back to 8-slice illustration 100 of FIG. 5, numerous board designs may be provided that incorporate essentially any overall z-coverage, and any number of slices in z-direction 21. For instance, as discussed a board may be designed that is dedicated to an 8-slice configuration, and another board may be designed that is dedicated to a 16-slice configuration. However, additional board designs may include 32, 64, or any number of slices, according to the invention.

As illustrated in FIG. 3, a limited number surfaces 52 (i.e., from 5 modules 20) are presented that are orthogonal to focal spot 54. This is in contrast to a more conventional system that may include, for instance, 57 modules. In a conventional system, because the number of modules is much greater than the 5 illustrated in FIG. 3, typically the angular correction from the outermost portions of the modules is small, and thus unaccounted for. That is, in order to cover FOV 58 with 57 modules, each module includes pixels having a small enough angle with respect to focal spot 54 so as to make the angle negligible. However, when the number of modules decreases to for instance 5 modules, outermost channels of each module include significant angles that can be accounted for in acquired imaging data, according to the invention. For instance, referring back to FIG. 3, one module 78 includes a ray 80 from focal spot 54 that is orthogonal to surface 52 and impinges approximately on a centermost channel of module 78. Thus, at the extreme edges of module 78, rays 82 impinge module 78 at angles 84 that are significantly (from an imaging data point of view) different from a 90° angle. Thus, data obtained within modules 20 may be geometrically corrected to account for the measurable geometric effect of modules that are significantly wider than modules in a system having 57 modules.

Figure 6:
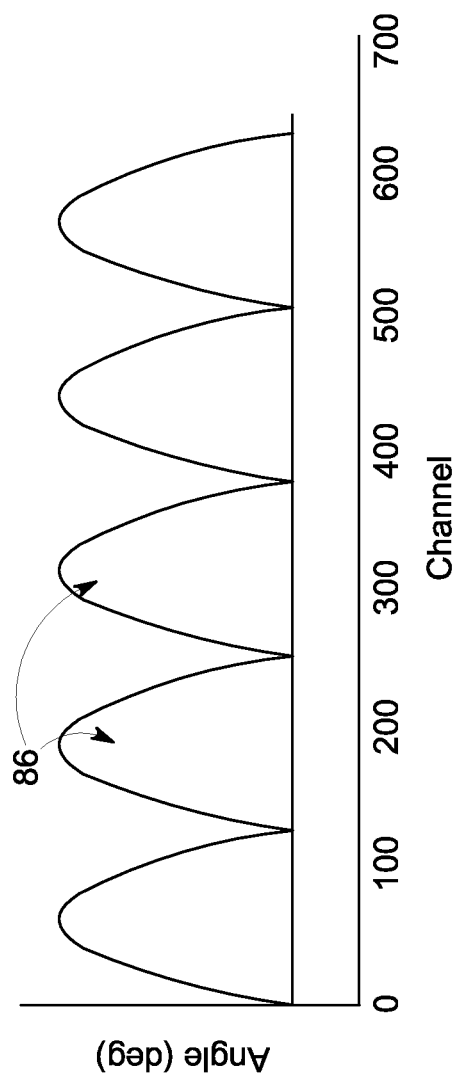
FIG. 6 illustrates a set of curves representing a geometric amount of correction for modules installed according to an embodiment of the invention.

Thus, referring to FIG. 6, a set of 5 curves 86 are illustrated that represent an angular amount of correction that corresponds to the physical and geometrical angle that results from modules 20 of FIG. 3 along channel direction 23. As one skilled in the art will recognize, the angle of correction for each modules, occurring as it corresponds to surfaces 52 of FIG. 3, is a function of parameters that include but are not limited to a width of each module, their distance from the focal spot, total number of channels in each module, and the like. Thus, according to the invention, acquired data may have a geometric correction associated therewith that is calculable based on representative curves 86 and based on the foregoing discussion.

Figure 7:
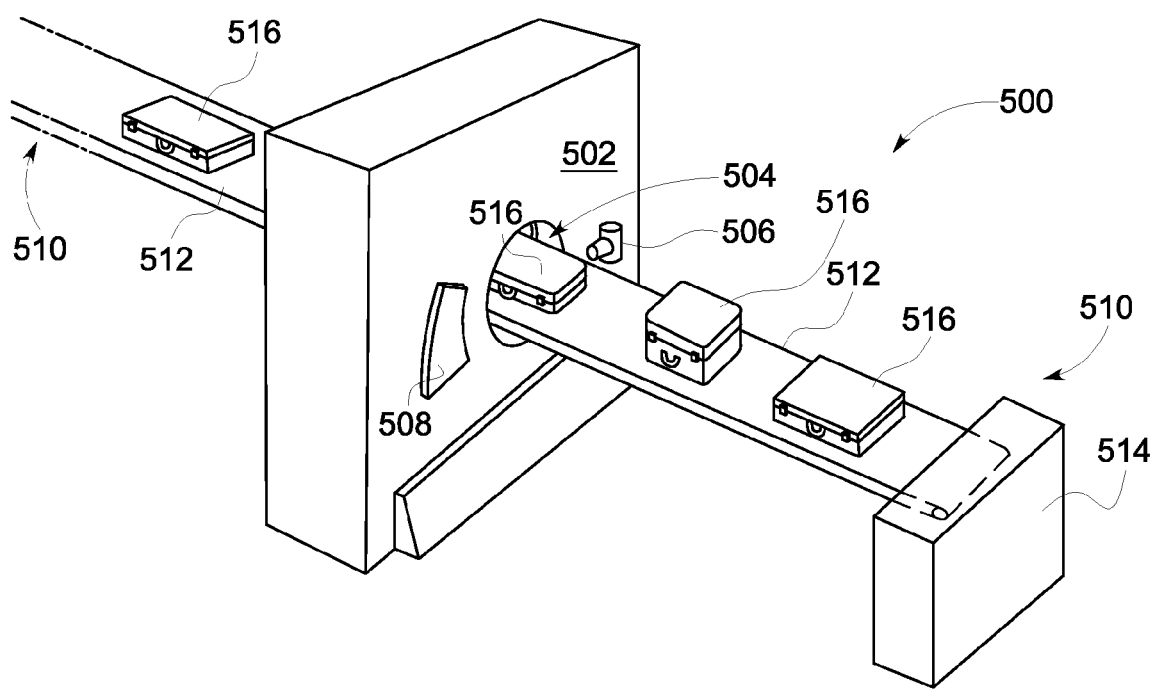
FIG. 7 is a pictorial view of a CT system for use with a non-invasive package inspection system.

Referring now to FIG. 7, package/baggage inspection system 500 includes a rotatable gantry 502 having an opening 504 therein through which packages or pieces of baggage may pass. The rotatable gantry 502 houses a high frequency electromagnetic energy source 506 as well as a detector assembly 508 having scintillator arrays comprised of scintillator cells similar to that shown in FIGS. 1 and 2. A conveyor system 510 is also provided and includes a conveyor belt 512 supported by structure 514 to automatically and continuously pass packages or baggage pieces 516 through opening 504 to be scanned. Objects 516 are fed through opening 504 by conveyor belt 512, imaging data is then acquired, and the conveyor belt 512 removes the packages 516 from opening 504 in a controlled and continuous manner. As a result, postal inspectors, baggage handlers, and other security personnel may non-invasively inspect the contents of packages 516 for explosives, knives, guns, contraband, etc.

A technical contribution for the disclosed method and apparatus is that it provides for a computer implemented method and apparatus of maintaining image quality while reducing system fabrication cost.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

According to an embodiment of the invention, a CT system includes a rotatable gantry having an opening to receive an object to be scanned, the rotatable gantry having a detector mounting surface, an x-ray source attached to the gantry and configured to project an x-ray beam toward the object, a plurality of detector modules each mounted within one field-of-view (FOV) and mounted directly to the detector mounting surface of the rotatable gantry, a data acquisition system (DAS) configured to receive outputs from at least one of the plurality of detector modules, and a computer programmed to acquire projections of imaging data of the object from the DAS, and generate an image of the object using the imaging data.

According to another embodiment of the invention, a method of fabricating a CT system includes fabricating a gantry having a detector mounting surface, attaching an x-ray source to the gantry such that x-rays emit from the x-ray source and through the rotational axis, and attaching, within one field-of-view (FOV), each detector module directly to the detector mounting surface such that the x-rays also emit to the two or more detector modules.

According to another embodiment of the invention, a CT detector module includes an electronics board, a first mounting surface, and a second mounting surface; wherein the first mounting surface is configured to be mounted directly onto a rotatable gantry of a CT system, the second mounting surface is configured such that the electronics board is mounted orthogonal with respect to x-rays emitted from an x-ray source that is positioned on the rotatable gantry.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A computed tomography (CT) system comprising:
   a rotatable gantry having an opening to receive an object to be scanned, the rotatable gantry having a detector mounting surface;
   an x-ray source attached to the gantry and configured to project an x-ray beam toward the object;
   a plurality of detector modules each mounted within one field-of-view (FOV) and mounted directly to the detector mounting surface of the rotatable gantry;
   a data acquisition system (DAS) configured to receive outputs from at least one of the plurality of detector modules; and
   a computer programmed to:
      acquire projections of imaging data of the object from the DAS; and
      generate an image of the object using the imaging data;
   wherein each of the plurality of detector modules comprises:
      an L-shaped mounting bracket having a first leg and a second leg, wherein the first leg is attached to the detector mounting surface of the rotatable gantry;
      a collimator array attached to the second leg of the L-shaped mounting bracket;
      an electronics board attached to both the second leg of the L-shaped mounting bracket and the collimator array, the electronics board being attached to an underside of the second leg that is opposite from a surface of the second leg at which the x-ray beam strikes the detector module; and
      analog to digital (A/D) application specific integrated circuit (ASIC) conversion chips attached to the electronics board that generate digital signals to be provided as the outputs from the detector module.

2. The CT system of claim 1 wherein the computer is programmed to geometrically correct for an angular position of pixels within one of the plurality of detector modules that is a function of their position along a channel direction of the CT system.

3. The CT system of claim 1 wherein the detector mounting surface is orthogonal to a rotational axis of the rotatable gantry.

4. The CT system of claim 1 wherein the one detector module is mounted such that the second leg is generally orthogonal to x-rays passing thereto from the x-ray source.

5. The CT system of claim 1 comprising:
   a diode array coupled to the electronics board, the diode array comprised of one or several frontlit diode array or a backlit diode array; and
   a scintillator coupled to the diode array.

6. The CT system of claim 5 wherein the electronics board comprises a configurable board configured to accommodate an array of scintillator-diode array pairs of varying sizes, such that a desired slice width can be achieved using a common electronics board architecture, with the electronics board being configured such that the CT system includes optionally both of the following arrays:
   the diode array coupled to the electronics board having a first amount of pixels in a slice direction and a first electronics readout capability of the DAS that corresponds with the first amount of pixels; or
   the diode array coupled to the electronics board having a second amount of pixels, twice that of the first amount of pixels, in the slice direction and a second electronics capability of the DAS that corresponds with the second amount of pixels.

7. The CT system of claim 1 further comprising a heat sink attached to the electronics board.

8. The CT system of claim 7 comprising a cover attached to the electronics board and configured to cover all of the A/D ASIC conversion chips and the heat sink.

9. A method of fabricating a computed tomography (CT) system comprising:
   fabricating a gantry having a detector mounting surface;
   attaching an x-ray source to the gantry such that x-rays emit from the x-ray source and through a rotational axis;

fabricating each of a plurality of detector modules configured to receive the x-rays from the x-ray source, wherein fabricating each of the plurality of detector modules comprises:
  providing an L-shaped mounting bracket comprising a first leg and a second leg;
  attaching a collimator array to the second leg;
  attaching an electronics board to the second leg and to the collimator array, with the electronics board securing the collimator array to the second leg;
  coupling a diode array comprised of several frontlit diode arrays or backlit diode arrays to the electronics board such that the x-rays pass generally orthogonal to a surface of the diode array; and
  coupling a scintillator to the surface of the diode array; and
attaching, within one field-of-view (FOV), each of the plurality of detector modules directly to the detector mounting surface such that the x-rays also emit to the detector modules, with a module mounting surface of the first leg being attached to the detector mounting surface;
wherein the electronics board is attached to the second leg and to the collimator array such that the electronics board is generally orthogonal to x-rays passing there through and from the x-ray source; and
wherein the collimator array is aligned lengthwise with the second leg, being positioned at an end of the second leg opposite from where the second leg is joined to the first leg.

10. The method of claim 9 comprising:
configuring a DAS incorporated in the detector module to acquire image projection data of the object; and
programming a computer to geometrically correct an angular position of the acquired image projection data as a function of a position along a channel direction of the CT system.

11. The method of claim 9 comprising, when the gantry is rotated about a rotational axis and about an object to be imaged, the detector mounting surface is at a right-angle to the rotational axis.

12. The method of claim 9 comprising configuring the electronics board as a configurable board designed to accommodate an array of scintillator-diode array pairs of varying sizes, such that a desired slice width can be achieved using a common electronics board architecture, such that the CT system includes optionally:
  the diode array coupled to the electronics board having a first amount of pixels in a slice direction and a first electronics readout capability of a DAS that corresponds with the first amount of pixels; or
  the diode array coupled to the electronics board having a second amount of pixels, twice that of the first amount of pixels, in the slice direction and a second electronics capability of the DAS that corresponds with the second amount of pixels.

13. A computed tomography (CT) detector module comprising:
  a collimator array;
  an electronics board;
  analog to digital (A/D) application specific integrated circuit (ASIC) conversion chips; and
  an L-shaped mounting bracket having a first leg and a second leg;
  wherein the first leg is configured to be mounted directly onto a rotatable gantry of a CT system;
  wherein each of the electronics board and the collimator array is mounted on the second leg so as to be positioned orthogonal with respect to x-rays emitted from an x-ray source that is positioned on the rotatable gantry, the collimator array being mounted on the second leg so as to be aligned lengthwise therewith and positioned at an end of the second leg opposite from where the second leg is joined to the first leg; and
  wherein the A/D ASIC conversion chips are mounted on the electronics board, with the A/D ASIC conversion chips performing an analog to digital conversion of electrical signals generated by the CT detector module responsive to x-rays received thereby.

14. The CT detector module of claim 13 comprising:
several diode arrays coupled to a surface of the electronics board such that a planar surface of the diode array is orthogonal to the x-rays emitted from the x-ray source; and
a scintillator coupled to the planar surface of the diode array.

15. The CT detector module of claim 14 wherein the first mounting surface is an x-y planar surface of the rotatable gantry, and the second mounting surface is orthogonal to the first mounting surface.

16. The CT detector module of claim 14 wherein:
the diode array is one of a frontlit diode array and a backlit diode array; and
when the diode array is a backlit diode array, the attachment of the diode to the board is achieved by conductive epoxy joints and when the diode array is frontlit, the connection to the board is achieved by wirebonds.

17. The CT detector module of claim 14 wherein the electronics board comprises a configurable board designed to accommodate an array of scintillator-diode array pairs of varying sizes, such that a desired slice width can be achieved using a common electronics board architecture, such that each module comprises several diode arrays to achieve 8 or 16 slices by 64 or 128 or more channels on a flat surface, defined by the electronics board.

* * * * *